（12) United States Patent
Wang et al.

(10) Patent No.: US 7,642,506 B2
(45) Date of Patent: Jan. 5, 2010

(54) PHANTOM FOR RADIOLOGICAL SYSTEM CALIBRATION

(75) Inventors: Xiaohui Wang, Pittsford, NY (US); Michael K. Rogers, Mendon, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 11/550,453

(22) Filed: Oct. 18, 2006

(65) Prior Publication Data

US 2008/0093544 A1      Apr. 24, 2008

(51) Int. Cl.
*G01B 13/00* (2006.01)
*G01N 23/02* (2006.01)
*A61B 6/02* (2006.01)

(52) U.S. Cl. ................. 250/252.1; 250/505.1; 378/207; 378/18

(58) Field of Classification Search ............... 378/18
See application file for complete search history.

(56) References Cited

U.S. PATENT DOCUMENTS

| | | | |
|---|---|---|---|
| 4,951,305 A * | 8/1990 | Moore et al. ................ | 378/147 |
| 5,406,612 A * | 4/1995 | Galkin ......................... | 378/207 |
| 5,420,441 A | 5/1995 | Newman et al. | |
| 5,910,975 A * | 6/1999 | Floyd et al. ................ | 378/207 |
| 6,409,383 B1 | 6/2002 | Wang et al. | |
| 6,694,047 B1 * | 2/2004 | Farrokhnia et al. .......... | 382/132 |
| 7,339,159 B2 * | 3/2008 | Juh et al. ................... | 250/252.1 |
| 2003/0072409 A1 * | 4/2003 | Kaufhold et al. .............. | 378/53 |

OTHER PUBLICATIONS

Polyimide (PI) Plastic Resin [online]. Ides—The Plastics Web, 2006 [retrieved on Jan. 23, 2008]. Retrieved from the Internet: <URL: www.ides.com/generics/PI.htm>.*

* cited by examiner

*Primary Examiner*—David P Porta
*Assistant Examiner*—Yara B Green

(57) ABSTRACT

A phantom for use in measuring characteristics of a digital radiography imaging system has at least one substrate having a patterned foil layer. The pattern in the foil layer being defined by a plurality of apertures within which the substrate is exposed.

17 Claims, 6 Drawing Sheets

PHANTOM FOR RADIOLOGICAL SYSTEM CALIBRATION

FIELD OF THE INVENTION

This invention generally relates to quality assurance (QA) for digital radiography imaging systems and more particularly relates to a phantom for obtaining quantitative measurement of characteristics of storage phosphor-based computed radiography (CR) imaging systems and direct-digital flat-panel detector-based direct radiography (DR) imaging systems.

BACKGROUND OF THE INVENTION

There are a number of parameters that, taken together, characterize the performance of x-ray imaging systems. For computed radiography (CR) and direct or digital radiography (DR) systems, these parameters can include spatial resolution, noise, detector efficiency, exposure response, dark image signal level, and image artifacts.

With CR and DR systems, the modulation transfer function (MTF) of the imaging system is often used to characterize the system's contrast and spatial resolution. MTF is a 2D (two-dimensional) function of spatial frequency and is usually measured for both x and y directions of the acquired image. Techniques for MTF measurement may employ a target or phantom, an angular slit, or an angular edge. A resolution target may employ a commercially available bar-target or a star-pattern target, for example. Alternately, a custom-made bar target of varying resolution, such as described in U.S. Pat. No. 5,420,441 entitled "Automatic Technique for Calibrating A Storage Phosphor Reader" to Newman et al., can be used. MTF can be estimated either using a human observer to identify the blur frequency point of the target or calculating the visibility modulation. The error of the estimation depends on the orientation/resolution of the target and on subjective criteria of the observer. This assessment requires that the target be perfectly aligned in the x or y direction, and the severity of the error increases when the target resolution is close to the Nyquist frequency of the imaging system.

Still other methods use a narrow slit to measure the line spread function, followed by Fourier transformation to obtain the MTF of the imaging system in the slit transverse direction. The slit, much narrower than the sampling pitch (pixel size) of the imaging system and long enough to cover at least one pixel in the slit transverse direction, is oriented at a slight angle to the y or x direction in order to achieve super sampling for aliasing reduction. Although it can provide a MTF measurement, this method relies on a delicately made, expensive slit target. Yet another method, used with some digital radiography imaging systems, uses a sharp and straight edge target to measure the edge spread function of the imaging system. The MTF in the edge transverse direction can be obtained from the edge spread function by taking the Fourier transform of its derivative.

The noise of the imaging system determines the system low-contrast resolution as well as the x-ray detective efficiency etc. The noise characteristics can be described by the noise power spectrum (NPS) of the imaging system, which is also a 2D function of spatial frequency. To obtain the NPS, a flat image region is generally used for Fourier analysis. Because the system noise level is also x-ray exposure dependent, the NPS is often measured at a certain exposure level to facilitate comparison between imaging systems.

Detective efficiency at each point (u, v) is a secondary parameter of the imaging system that can be readily calculated from the system MTF and NPS:

$$DQE(u, v) \sim \frac{MTF^2(u, v)}{NPS(u, v)}$$

Response accuracy, linearity, and uniformity are among the parameters for characterizing exposure response, the relationship between the output of the imaging system (image pixel values) and the incident x-ray exposure. Ideally, the exposure response or logarithmic exposure response should be linear and equal for all the pixels across the whole image. Exposure accuracy and linearity describe how accurately and linearly the output of the imaging system can track the incident x-ray exposure. Response uniformity describes the inter-pixel response variation. Each of these parameters is usually measured using the same x-ray spectrum, but at different exposure levels.

The dark image signal level determines the baseline noise of the imaging system and is independent of x-ray exposure. For a CR image, this corresponds to the signal level that would result from reading an erased phosphor screen, and for a DR image, this corresponds to the accumulated noise level before the x-ray exposure and during the readout process.

Artifacts in images are often unpredictable and may take the form of spots, lines and low-frequency modulations, either periodic or non-periodic. White and dark spot artifacts are usually caused by foreign dust/dirt residing on the image receptor or may be caused by bad pixels (within a DR detector). There are two major types of line artifacts, periodic (banding), and non-periodic (streaks). Either artifact, given enough magnitude, can result in objectionable image quality.

Other parameters for image quality that are unique to CR imaging include scan linearity and scan accuracy. For a CR imaging system, a laser beam provides raster scanning for reading the signal from the storage phosphor screen. Because there are moving optical devices, the image pixel size and the pixel aspect ratio can exhibit a degree of spatial variation. Scan accuracy gives a measure of the geometric integrity of the image.

Although there is no variable geometry related quality assurance issues for DR, since the imaging pixels are solid state elements manufactured on an evenly distributed grid, the locations of failed pixels and the individual pixel response correction are unique to DR and need to be characterized as part of the calibration process.

Because there are a number of diverse parameters to be measured for maintaining image quality in digital x-ray imaging systems, the image quality and Quality Assurance (QA) process presents a challenge for designing a quick, accurate, easy to use, and fully automatic method/procedure to conduct the measurements. In general, most of the proposed methods for QA testing rely either on visually reading image pixel values from a computer screen or on printing a test image on film and then using visual examination combined with film densitometer measurements. However, as noted in commonly assigned U.S. Pat. No. 6,409,383 entitled "Automated And Quantitative Method For Quality Assurance Of Digital Radiography Imaging Systems" to Wang et al., existing methods are limited by the quality of the film printer and densitometer. Other methods can be relatively difficult and time-consuming.

Automated methods, such as that disclosed in commonly assigned U.S. Pat. No. 5,420,441 entitled "Automated Technique For Calibrating A Storage Phosphor Reader" to Newman et al., often employ a patterned target or phantom. Specially made for this type of testing, the phantom is imaged in a test sequence. Then, analysis of the phantom image is performed to derive system performance parameters. These derived parameters can then be compared with corresponding pre-stored threshold values of a normal imaging system.

Radiography phantoms of various types have been disclosed. For example, commonly assigned U.S. Pat. No. 6,409,383 entitled "Automated and Quantitative Method for Quality Assurance of Digital Radiography Imaging Systems" to Wang et al., discloses a phantom formed from a rigid copper sheet having a pattern of milled or punched apertures. This phantom, designed for use with cassettes of various dimensions, is designed for general radiography systems having x-ray tube voltage in the 60-130 kVp range.

By comparison with general radiography systems, mammography systems operate at a lower x-ray tube voltage range. Typical x-ray tube voltage for mammography imaging is in the range of 25-35 kVp. As is well known, lower kVp x-rays are more easily attenuated than are rays in a higher range. Therefore, a phantom for a general radiography system, such as that disclosed in the '383 Wang et al. patent, is not suitable for use with the mammography system because the attenuation of the phantom is too high. Instead, a phantom designed for mammography systems must have substantial portions that are permeable to substantially lower kVp levels.

Phantoms especially designed for the lower exposure levels of mammography have been developed. For example, one known mammography phantom, the Artinis Contrast-Detail Phantom, from Artinis Medical Systems, Zetten, The Netherlands, employs an array of gold discs having increasing thicknesses and diameters. The deposited gold discs are distributed on an aluminum base and encased within a PMMA (Polymethyl methacrylate) cover. However, because this type of phantom uses precious metals deposited in dots of exacting thicknesses and diameters, it is difficult to fabricate and is very expensive.

One principle for phantom design relates to the overall response region of the imaging system detector. It is desired that the phantom be designed to show system sensitivity over the linear response region of the system under test. At the same time, such a phantom should be reasonably robust, so that it can be handled and used repeatedly for testing and calibrating the mammography system. In CR mammography imaging, the X-ray cassette that is used has a directional bias; the imaged tissue is intended to lie on the side of the cassette that is nearest to the chest wall of the patient. Thus, a phantom designed for such a system should be particularly arranged with the same directional bias to provide the optimal measurement conditions for breast tissue imaging. Lower cost solutions would be particularly advantageous.

Thus, it can be appreciated that there is a need for a phantom that is configured for the demands of the mammography system and is relatively robust and capable of supporting automated calibration of the mammography imaging apparatus.

SUMMARY OF THE INVENTION

It is an object of the present invention to provide a phantom for use in measuring characteristics of a digital radiography imaging system comprising at least one substrate having a patterned foil layer, wherein the pattern defines a plurality of apertures within which the substrate is exposed.

It is a feature of the present invention that the phantom can be designed for suitable radiation absorption levels for mammography imaging calibration.

It is an advantage of the present invention that it can provide a phantom for mammography that is robust, reusable, and capable of supporting automated system calibration.

These and other objects, features, and advantages of the present invention will become apparent to those skilled in the art upon reading the following detailed description, when taken in conjunction with the drawings wherein there is shown and described an illustrative embodiment of the invention.

According to one aspect of the present invention, there is provided a phantom for use in measuring characteristics of a digital radiography imaging system. The phantom includes at least one substrate having a patterned foil layer. The pattern in the foil layer is defined by a plurality of apertures within which the substrate is exposed.

According to another aspect of the present invention, there is provided a phantom for use in measuring characteristics of a digital radiography image system. The phantom includes first and second patterned sheets. The first patterned sheet includes a first substrate layer and a first foil layer coupled to the first substrate layer. The second patterned sheet includes a second substrate layer and a second foil layer coupled to the second substrate layer. The first foil layer includes a pattern that exposes a portion of the first substrate layer. The pattern comprises a first aperture formed near an outer portion of the first patterned sheet, and a second aperture spaced from the outer portion of the first patterned sheet. The first aperture is of a first size, and the second aperture is of a second size larger than the first size. The first and second patterned sheets are stacked together to form a substantially flat plate that defines, in the path of incident radiation, a phantom pattern comprising: a plurality of apertures having no foil layer, at least one area having a single foil layer, and at least one area having a foil layer thicker than the single foil layer.

DETAILED DESCRIPTION OF THE INVENTION

It is to be understood that elements not specifically shown or described hereinbelow may take various forms well known to those skilled in the art.

Figure 1:
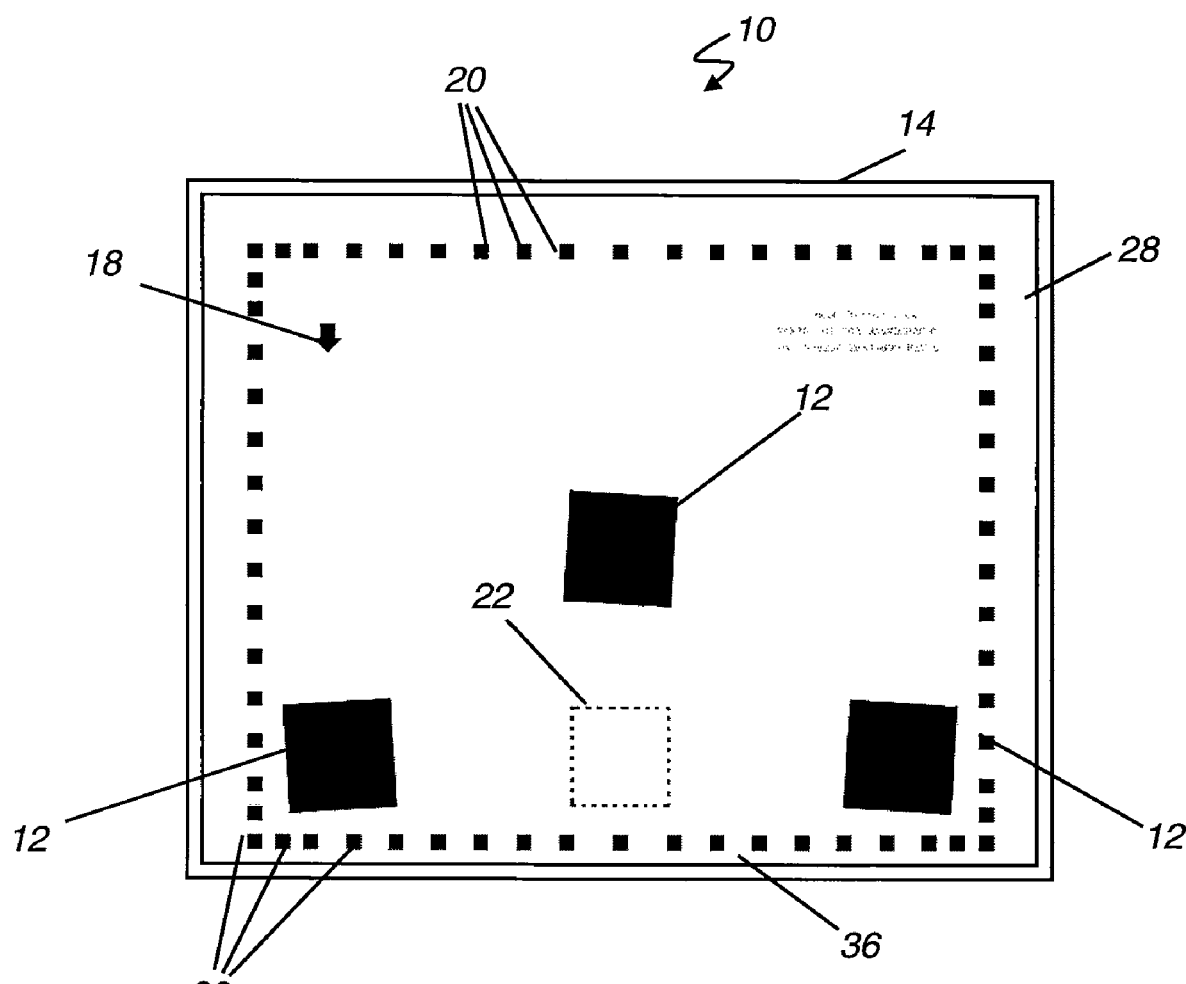
FIG. 1 is a plan view showing the pattern of areas on a phantom in one embodiment of the present invention.

According to one aspect, the present invention adapts techniques that have been used in printed circuit-board (PCB) fabrication and uses these techniques to form a phantom for mammography imaging. Referring to FIG. 1, there is shown a phantom 10 according to the present invention. Phantom 10 is comprised of one or more sheets of a substrate 36, whose surface has a patterned metallic foil coating, with thickness and overall geometry of the pattern designed for the relatively low kVp levels and spatial characteristics of mammography. The substrate material is preferably a material exhibiting minimal attenuation to x-rays, with attenuation in the approximate range of plastic materials.

The view shown in FIG. 1 is a negative representation, wherein the dark areas represent areas where metallic foil has been etched away to expose the underlying substrate 36 material; a plated area 28 of metal foil deposited on substrate 36 is represented in white in this figure. An arrangement of apertures 12 and 20 is provided, with one set of apertures 20 distributed near the periphery of phantom 10 toward one side and at least one larger aperture 12 that lies toward the center.

Phantom 10 has an orientation mark 18 used for positioning this device/apparatus in a mammography system. An arrow is used as orientation mark 18 in the embodiment shown in FIG. 1, pointing toward the region that corresponds to the chest wall of a patient during mammography imaging. With reference to the view of FIG. 1, the lower edge of phantom 10 corresponds to the chest wall side of the patient. This edge would be placed toward the chest wall side with respect to the image detector of the radiography system. The distribution of apertures 12 and 20 is skewed to this side of phantom 10, exposing a higher percentage of the underlying substrate 36 along that portion of phantom 10 lying closer to the chest wall edge than lying toward the opposite edge. A frame 14 is provided for stiffening phantom 10 so that it effectively forms a flat plate when used with the imaging apparatus.

Phantom 10 is configured to provide a pattern of apertures having very low attenuation and a metal foil coating of various thicknesses for mammography calibration. Relative to the plan view of FIG. 1, radiation is incident normal to the page. A double layer area 22 (e.g., an area of increased thickness), indicated in dotted outline in FIG. 1, presents an area of increased thickness, such as a double thickness, of metallic coating to the incident radiation. In one embodiment, as described subsequently, this additional thickness is afforded by using a stacked sheet arrangement. Plated area 28 (outside of the boundary of area 22) presents a single thickness of metallic coating to incident radiation. Apertures 12 and 20 provide areas having no metallic coating, exposing substrate 36 so that only the substrate material is in the path of the incident radiation in these areas. Apertures 12 can be skewed at one or more angles relative to the edges of phantom 10. This arrangement is advantaged for MTF and high-resolution aliasing detection. Gradient areas could also be provided within apertures 12.

Apertures 12, defined by the patterned foil layer, also have a layout that enables the MTF response to be readily measured at different locations in the image area. In a preferred embodiment, the MTF response is measured near the beginning, middle, and end of the laser scan direction in order to check the laser focus across the whole scan width (e.g., running in the left-to-right direction in the view of FIG. 1). As shown in the embodiment of FIG. 1, some of the apertures can have edges that are oblique, that is, not perpendicular or parallel in the plane with respect to edges of other apertures or with edges of phantom 10 itself. This optional arrangement can be advantageous for MTF evaluation.

In general, phantom 10 is arranged to provide a reference target that measures system imaging characteristics, including MTF, exposure response (both accuracy and linearity), geometric distortion, and noise. For CR systems, geometry-related parameters such as pixel size, aspect ratio, scan tilt, scan linearity and accuracy are obtained by measuring the locations of predefined landmarks in the phantom image. For DR systems, on the other hand, these landmarks have limited utility.

Figure 2:
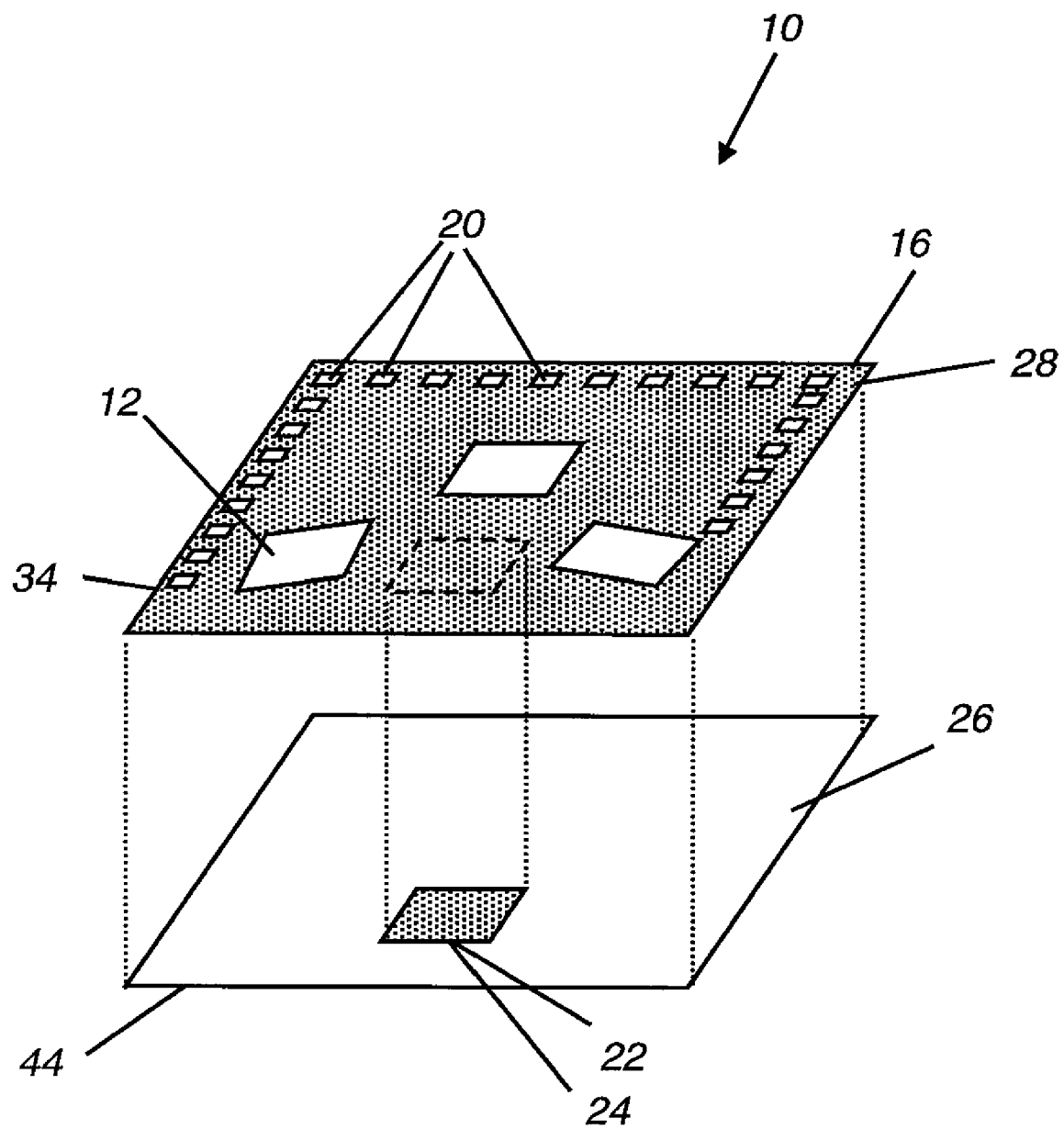
FIG. 2 is an exploded orthogonal view showing one arrangement for layers that form the phantom of the present invention.

FIG. 2 shows how phantom 10 can be formed from stacked sheets. In this figure, the darkened areas indicate areas having a metallic coating (for example, plated areas 24 and 28) on corresponding substrate layers 34 and 44. An upper sheet 16 has apertures 12 and 20 formed in it. Sheet 16 is overlaid onto a lower sheet 26 that has only a small plated area 24, used to combine with plated area 28 on upper sheet 16 to form double layer area 22 when sheets 16 and 26 are stacked.

Figure 3:
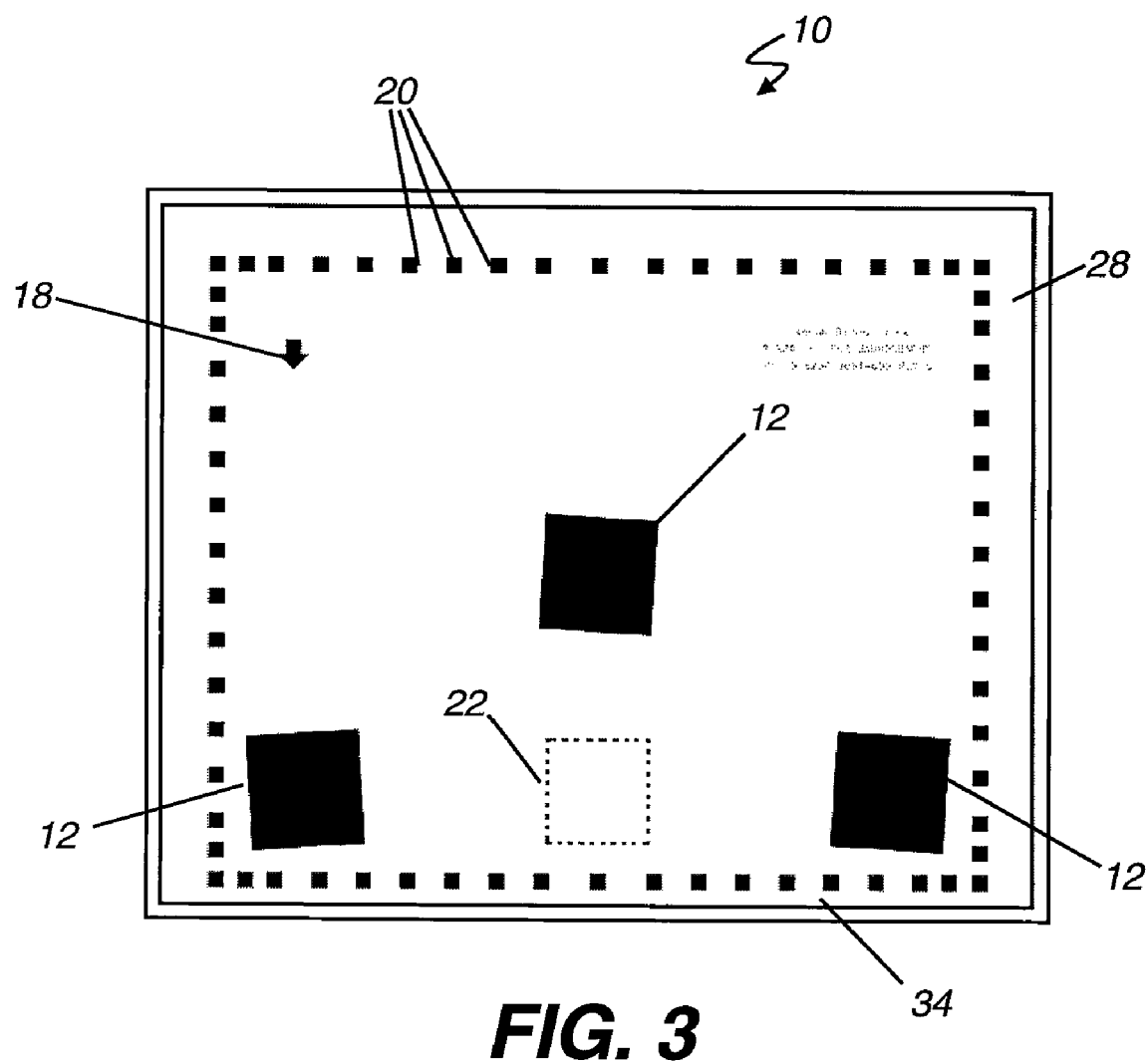
FIG. 3 is a plan view showing the arrangement of one patterned sheet in one embodiment.
Figure 4:
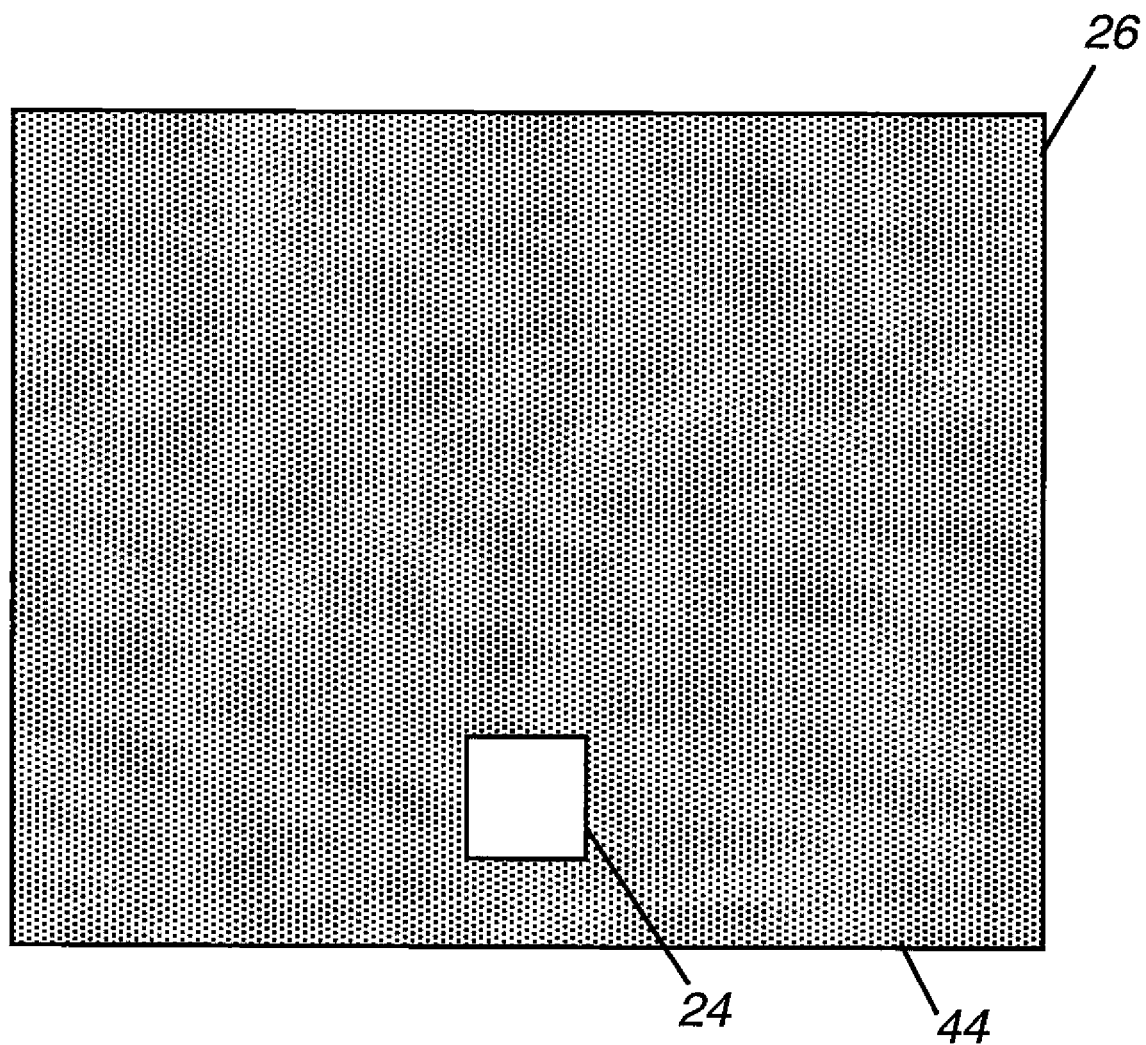
FIG. 4 is a plan view showing the arrangement of a second patterned sheet.

FIGS. 3 and 4 show the individual sheets 16 and 26, respectively. In FIGS. 3 and 4, as in FIG. 1, shaded/darker areas indicate etched areas, that is, areas where the metal foil/coating is removed and substrate layer 34 or 44 is exposed.

Figure 5:
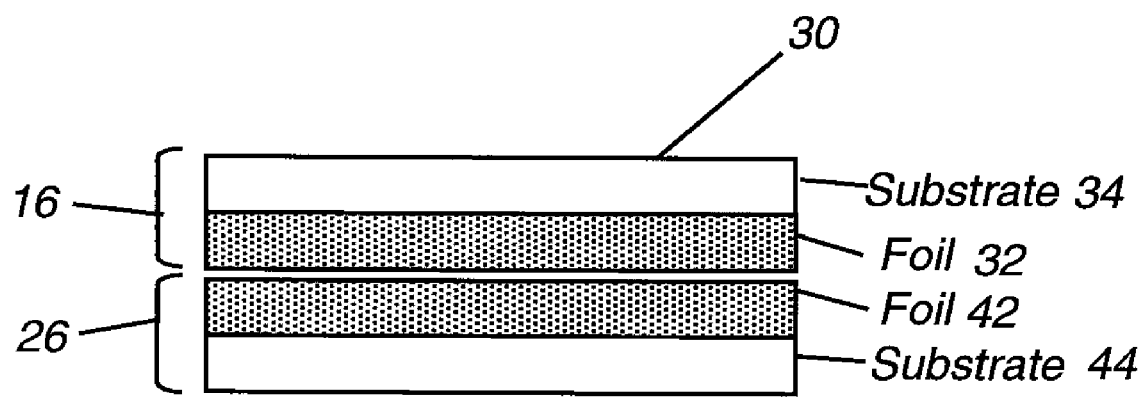
FIG. 5 is a cross-sectional view showing an arrangement of layers in one embodiment.

FIG. 5 shows a cross-sectional view, illustrating how sheets 16 and 26 are formed and stacked atop each other in one embodiment. Sheet 16 has substrate layer 34 and an attached foil layer 32. Foil layer 32 can be deposited onto substrate layer 34 or can be adhesively bound to substrate layer 34, so that an additional thin coating of adhesive (not shown in FIG. 5) lies between foil layer 32 and its substrate layer 34. Similarly, adhesive can be used between a foil layer 42 and substrate layer 44 for sheet 26. Adhesive can also be applied in order to bond sheets 16 and 26 together.

FIG. 5 shows metal-to-metal bonding between sheets 16 and 26; however, it can be appreciated that other arrangements are possible. Moreover, this arrangement is generally most advantageous for measuring response to phantom edges more precisely.

Fabrication is now described.

The present invention allows the use of conventional PC board photochemical etching procedure for forming patterned layers 16 and 26 of phantom 10. This type of method is advantaged since it allows very well-defined edges to be formed for apertures 12 and 20 in relatively thin metallic layers. Other possible options for metal removal include laser etching, for example. The pattern that is formed on layers 16 and 26 could alternately be fabricated using other deposition methods, such as printing for example. For an embodiment using two patterned sheets 16 and 26, as shown in FIG. 2, different fabrication methods could be used for each sheet.

Phantom 10 of the present invention can be formed using any of a number of different materials. In one embodiment, the substrate material used is a plastic or polymer film such as Kapton® polyimide film, a product of DuPont, Wilmington, Del. Kapton polyimide film exhibits good dimensional stability over a wide temperature range and has been widely used for flexible printed circuit components. Polyimide is particularly noted for its suitability in high radiation environments, exhibiting a low absorption rate for x-rays and minimal scattering at small angles.

Copper is one of a number of metals that can be used for foil layers 32 and 42. Other possible metals for this purpose include aluminum and its alloys, as well as lead.

Typical thicknesses for metal foil are in the range of 0.0330 (+/−0.0025) inches in one embodiment using copper. However, the thickness of foil layers 32 and 42 is variable and can depend on the type of metal used and on the sensitivity range for which phantom 10 is designed. Where multiple thicknesses are stacked, such as those used to form double layer area 22, foil layers 32 and 42 may have equal thickness. However, there may be advantages in using different thicknesses for foil layers 32 and 42. The thickness of a Kapton substrate in one embodiment is approximately 0.076 inches. Typical attenuation values used in one embodiment are approximately 4× attenuation for foil layer 32 with attenuation of about 50× where foil layer 42 overlaps foil layer 32 over double-layer area 22. Substrates 34 and 44 exhibit essentially no attenuation.

With reference to the embodiment of FIG. 5, a wide range of adhesives could be used for bonding foil layers 32 and 42 to their respective substrate layers 34 and 44, as well as for bonding sheets 16 and 26 together. A modified acrylic adhesive is used for this purpose in one embodiment.

In the embodiment of FIG. 1, frame 14 helps to stiffen phantom 10, keeping its overall flatness within about 1 mm per square inch or better. Frame 14 can be formed from FR4 stiffener, a standard material made from epoxy and woven fiberglass and familiar to those skilled in the art of printed circuit board fabrication.

Alternate embodiments can be envisioned. The present invention allows a number of optional embodiments for forming phantom 10 that are suitable for lower-kVp radiography. In one embodiment, a sheet of polyimide substrate has a patterned foil coating on both sides, for example. Material types and dimensions, as well as the pattern or patterns formed in the metal foil layers, can be varied from those shown here, without departing from the scope of the present invention. In one alternate embodiment a single metal foil layer may be sandwiched between two layers of substrate.

It is noted that substrate materials that provide some amount of attenuation could alternately be used. Following general phantom design principles, there should be a significant difference between the attenuation of the substrate and that of its patterned metal foil layer.

An image processing procedure is now described.

Using phantom 10 according to the present invention allows the use of an automated procedure for performing calibration of a CR cassette or other radiological detection device. For example, the Wang et al. '383 disclosure cited above provides describes suitable image processing methods and techniques that can apply when using phantom 10.

Figure 6:
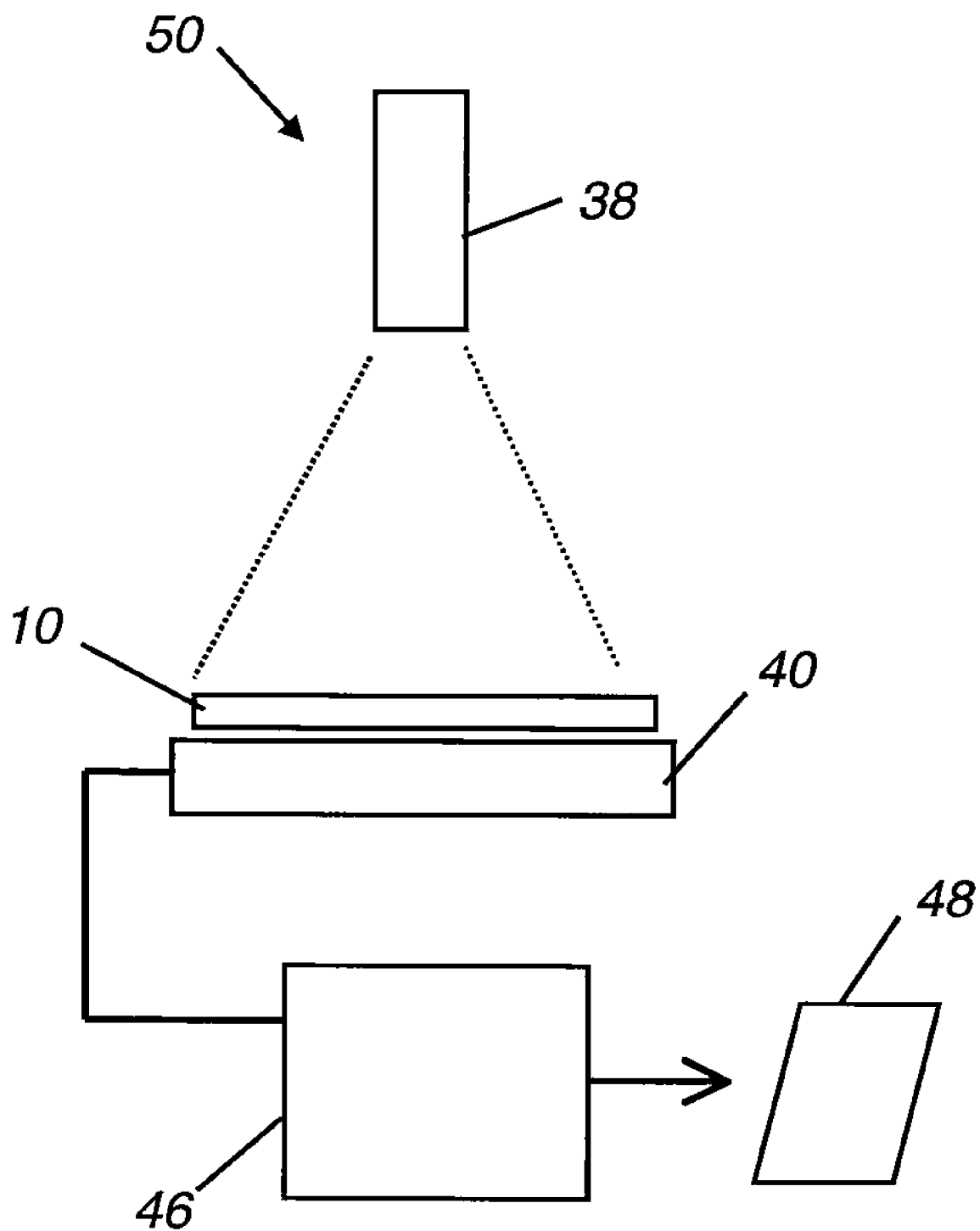
FIG. 6 is a block diagram showing the use of a phantom in a digital imaging system according to the present invention.

Unlike the phantom described in the Wang et al. '383 disclosure, which is metal having apertures that are drilled, milled, or otherwise formed, phantom 10 of the present invention uses a substrate having a patterned foil layer that is apertured to expose portions of an underlying substrate by a defined pattern of apertures. As shown in FIG. 6, phantom 10 is used in a digital mammography imaging system 50, placed by an operator or technician between a radiation source 38 and a radiation detector 40, such as a detector housed within a CR cassette or a DR detector. Image processing controlled by a control logic processor 46 is then used to provide an image 48 of phantom 10 that can be used to assess and adjust calibration for system 50.

It is noted that the term "foil" used herein is used in this disclosure in a broad sense, to indicate a relatively thin coating of metallic material that is coupled to a sheet of substrate in a manner in order to fabricate the phantom of the present invention. Coupling to the substrate can be performed before or after the pattern is formed. In general, it is assumed that this foil, on a single sheet, has a substantially consistent thickness, except over areas where it has been intentionally patterned to define apertures.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention. For example, while the overall pattern shown in FIGS. 1-4 has particular advantages for use with computed radiography (CR) mammography imaging, this pattern, as well as materials and thicknesses, could be modified for other types of imaging and other types of radiography imaging apparatus.

Thus, what is provided is an apparatus and method for obtaining quantitative measurement of characteristics of storage phosphor-based computed radiography (CR) imaging systems and direct-digital flat-panel detector-based direct radiography (DR) imaging systems.

PARTS LIST

| | |
|---|---|
| 10 | Phantom |
| 12 | Aperture |
| 14 | Frame |
| 16 | Sheet |
| 18 | Orientation mark |
| 20 | Aperture |
| 22 | Double-layer area |
| 24 | Plated area |
| 26 | Sheet |
| 28 | Plated area |
| 30 | Surface |
| 32 | Foil layer |
| 34 | Substrate layer |
| 36 | Substrate |
| 38 | Source |
| 40 | Detector |
| 42 | Foil layer |
| 44 | Substrate layer |
| 46 | Control logic processor |
| 48 | Image |
| 50 | Imaging system |

The invention claimed is:

1. A phantom for use in measuring characteristics of a digital radiography mammography imaging system comprising a plurality of stacked sheets, each sheet including a substrate of low x-ray attenuating material having up to one patterned foil layer disposed on a major surface thereof, the patterned foil layers oriented to face each other, each foil layer having a uniform thickness across the substrate and each pattern defining one or more etched apertures within which the substrate is exposed such that the patterned foil layers of the plurality of stacked sheets together form a composite metal foil of varying thickness without overlapping etched apertures.

2. The phantom according to claim 1 wherein the substrate is taken from the group consisting of plastic, glass, and fiberglass.

3. The phantom according to claim 1 wherein the patterned foil layer is a metal taken from the group consisting of copper, aluminum, aluminum alloys, and lead.

4. The phantom according to claim 1 wherein the distribution of apertures is such that a higher percentage of substrate is exposed toward a chest wall edge of the image detector than toward the opposite edge.

5. The phantom according to claim 1 further comprising a frame around the edges of the substrate.

6. The phantom according to claim 1 wherein the pattern comprises an orientation mark.

7. The phantom according to claim 1 wherein at least some of the apertures have edges that are at oblique angles with respect to edges of other apertures.

8. A phantom for use in measuring characteristics of a digital radiography mammography imaging system, comprising:

a) a first patterned sheet comprising:
(i) a first substrate layer;

(ii) a single foil layer having a uniform thickness coupled to the first substrate layer and having a pattern that exposes a portion of the first substrate layer, the pattern comprising: a first aperture formed near an outer portion of the first patterned sheet, and a second aperture spaced from the outer portion of the first patterned sheet, the first aperture being of a first size, the second aperture being of a second size larger than the first size; and b) a second patterned sheet comprising:
  (i) a second substrate layer;
  (ii) a single foil layer having a uniform thickness coupled to the second substrate layer;
  wherein the first and second patterned sheets are stacked together to form a substantially flat plate that defines, in a path of incident radiation, a phantom pattern comprising: a composite foil of varying thickness formed by the single foil layers of the first and second patterned sheets and including a plurality of apertures having no foil layer, at least one aperture having a single foil layer, and at least one aperture having more than a single foil layer, and wherein the patterned foil layers are oriented to face each other without overlapping of apertures.

9. The phantom of claim 8 wherein the first and second substrate layers comprise a polyimide film.

10. The phantom of claim 8 wherein the single foil layers comprise a metal taken from the group consisting of: copper, aluminum, aluminum alloys, and lead.

11. The phantom of claim 8 further comprising a frame for stiffening the first and second patterned sheets.

12. The phantom of claim 8 wherein the first patterned sheet further comprises an orientation mark.

13. The phantom according to claim 8 wherein the first and second substrate layers are taken from the group consisting of: plastic, glass, and fiberglass.

14. The phantom according to claim 8 wherein the first or second apertures have edges that are at oblique angles with respect to edges of other apertures.

15. The phantom according to claim 8 wherein the distribution of the first or second apertures on the single foil layer of the first patterned sheet is such that a higher percentage of the first substrate layer is exposed toward a chest wall edge of an image detector of the digital radiography imaging system than toward the opposite edge.

16. A phantom for use in measuring characteristics of a digital radiography mammography imaging system, comprising:
  a) at least one substrate;
  b) a single patterned foil layer of uniform thickness coupled to one major surface of the at least one substrate and including a pattern, the pattern defining a plurality of apertures within which the at least one substrate is exposed; and
  c) a single patterned foil layer of uniform thickness coupled to a facing major surface of the at least one substrate, wherein the single patterned foil layers together form a composite foil of varying thickness.

17. A method for fabricating a phantom for use in measuring characteristics of a digital radiography mammography imaging system, comprising:
  depositing a single metallic coating of uniform thickness on each of a pair of substrates, each substrate and associated single metal coating forming a sheet;
  etching a pattern of apertures in the single metallic coating of each sheet through which the substrate is exposed; and
  stacking the sheets to form the phantom such that the single metallic coatings of the stacked sheets mate to form a composite metal layer of varying thickness.

* * * * *